(12) United States Patent
Messerli et al.

(10) Patent No.: US 6,929,662 B1
(45) Date of Patent: Aug. 16, 2005

(54) END MEMBER FOR A BONE FUSION IMPLANT

(75) Inventors: Dominique D. Messerli, West Chester, PA (US); David C. Paul, Phoenixville, PA (US)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/497,123

(22) Filed: Feb. 3, 2000

Related U.S. Application Data (60) Provisional application No. 60/118,806, filed on Feb. 4, 1999.

(51) Int. Cl.⁷ .................................................. A61F 2/44
(52) U.S. Cl. .................................................. 623/17.11
(58) Field of Search ........................ 623/17.11, 17.12, 623/17.13, 17.14, 17.15, 17.16; 606/61, 72, 606/73

(56) References Cited

U.S. PATENT DOCUMENTS

| | | | |
|---|---|---|---|
| 4,497,419 A * | 2/1985 | Reitzel ........................ 220/302 |
| 4,820,305 A | 4/1989 | Harms et al. .................. 623/16 |
| 4,834,757 A | 5/1989 | Brantigan ..................... 623/17 |
| 4,961,740 A | 10/1990 | Ray et al. ..................... 606/61 |
| 5,015,247 A | 5/1991 | Michelson .................... 606/61 |
| 5,055,104 A | 10/1991 | Ray ............................. 606/61 |
| 5,192,327 A | 3/1993 | Brantigan ..................... 623/17 |
| 5,571,192 A | 11/1996 | Schönhöffer ................. 623/17 |
| 5,609,635 A | 3/1997 | Michelson .................... 623/17 |
| 5,609,637 A | 3/1997 | Biedermann et al. .......... 623/17 |
| 5,674,295 A | 10/1997 | Ray et al. ..................... 623/17 |
| 5,683,464 A * | 11/1997 | Wagner et al. ............. 623/17.16 |
| 5,700,291 A * | 12/1997 | Kuslich et al. ................ 606/96 |
| 5,702,449 A | 12/1997 | McKay ......................... 623/17 |
| 5,702,451 A | 12/1997 | Biedermann et al. .......... 623/17 |
| 5,702,455 A | 12/1997 | Saggar ......................... 623/17 |
| 5,755,798 A | 5/1998 | Papavero et al. .............. 623/17 |
| 5,776,197 A | 7/1998 | Rabbe et al. .................. 623/17 |
| 5,776,199 A | 7/1998 | Michelson .................... 623/17 |
| D397,439 S | 8/1998 | Koros et al. ................ D24/155 |
| 5,800,547 A | 9/1998 | Schäfer et al. ................ 623/17 |
| 5,827,328 A | 10/1998 | Buttermann ................... 623/17 |
| D403,069 S | 12/1998 | Drewry et al. .............. D24/155 |
| 5,860,973 A | 1/1999 | Michelson .................... 606/61 |
| 5,861,041 A | 1/1999 | Tienboon ...................... 623/17 |
| 5,865,845 A | 2/1999 | Thalgott ....................... 623/17 |
| 5,865,848 A | 2/1999 | Baker ........................... 623/17 |
| 5,972,031 A | 10/1999 | Biedermann et al. .......... 623/17 |

(Continued)

FOREIGN PATENT DOCUMENTS

DE 19509317 A1 9/1996

(Continued)

*Primary Examiner*—Brian E Pellegrino
(74) *Attorney, Agent, or Firm*—Jones Day (57) ABSTRACT

An end member for use with a bone fusion implant is disclosed. The end member has a first portion, a second portion, and a shoulder connecting the two portions. The second portion is sized to fit within the interior of the bone fusion implant in such a fashion that the shoulder rests on the edge of the implant. The top surface of the first portion has at least one slot to receive a surgical instrument such as an inserter and/or distractor to facilitate implantation of the end member and bone fusion implant. The top surface may also have teeth to provide initial mechanical stability between the bone and end plate and promote bone fusion.

28 Claims, 6 Drawing Sheets

U.S. PATENT DOCUMENTS

| | | | | |
|---|---|---|---|---|
| 5,980,522 A | * | 11/1999 | Koros et al. | 606/61 |
| 5,989,289 A | * | 11/1999 | Coates et al. | 623/17.16 |
| 5,989,290 A | | 11/1999 | Biedermann et al. | 623/17 |
| 6,015,436 A | | 1/2000 | Schönhöffer | 623/17 |
| 6,086,613 A | * | 7/2000 | Camino et al. | 623/17.16 |
| 6,143,033 A | * | 11/2000 | Paul et al. | 623/17.11 |
| 6,149,686 A | * | 11/2000 | Kuslich et al. | 623/17.11 |

FOREIGN PATENT DOCUMENTS

| | | | | |
|---|---|---|---|---|
| EP | 0 832 622 A2 | | 4/1998 | |
| EP | 0966 930 A1 | | 12/1999 | |
| RU | 2008851 | * | 3/1994 | 623/17 |
| WO | WO 96/37170 | | 11/1996 | |
| WO | WO 98/29047 | | 7/1998 | |
| WO | WO 99/32055 | | 7/1999 | |

* cited by examiner

END MEMBER FOR A BONE FUSION IMPLANT

CROSS-REFERENCE TO RELATED APPLICATIONS

Priority of Provisional application Ser. No. 60/118,806 filed on Feb. 4, 1999 is claimed under 35 U.S.C. § 119(e).

FIELD OF THE INVENTION

The present invention relates to a device for bone fusion, and in particular to an end member for a bone fusion implant.

BACKGROUND OF THE INVENTION

The treatment and management of bone defects remains one of the most challenging aspects of orthopaedics. Bone defects occur in a wide variety of clinical situations. Restoring natural anatomical length and shape of any long bone with a bone defect is problematic. Additionally, whenever a vertebra has to be removed, it is necessary to insert a vertebral spacer to restore the natural length and curvature of the spine as well as to promote bone fusion. Restoring spinal anatomy and stability and promoting bone fusion are even more difficult in a corpectomy, a surgical procedure in which a section of one or several vertebrae is removed.

Many different implants have been developed for use with bone defects. So-called "mesh implants" have shown to be particularly effective. One such implant is the SynMesh™ available from Synthes (USA) of Paoli, Penna. The SynMesh™ is a titanium mesh cylinder which is provided with a plurality of uniformly-spaced apertures of uniform size distributed on its surface. In order to address the different clinical situations in which bone defects arise, the SynMesh™ is available in a variety of lengths and diameters. Commercially available allografts for treating bone defects have recently become available.

Although the clinical results of mesh and allograft implants have generally been positive, one possible clinical complication is subsidence of the implant. Excessive sinking of the ends of the implant into the bone with which they contact is especially troublesome whenever the bone is extremely porous. From both a mechanical and physiological point-of-view, it would also be advantageous to increase the surface contact area between the implant and bone. U.S. Pat. No. 5,702,451 to Biedermann et al. discloses end rings that attempt to address these concerns. However, the end rings disclosed have no provisions for holding, insertion, and distraction instruments. Thus, implantation can be difficult. Furthermore, there can be excessive movement between the bone and the disclosed end rings after implantation. This may delay, and perhaps prevent bone fusion.

As the discussion above illustrates, there is a need for an improved end member for use with a bone fusion implant.

SUMMARY OF THE INVENTION

The present invention relates to an end member for use with a bone fusion implant for fusing portions of bone. The end member has a first portion, a second portion sized to be inserted into the bore of the implant, and a shoulder between the first and second portions. When the second portion is inserted into the bore, the shoulder rests on an edge of the implant. The top surface of the first portion conforms in size and shape with the bone and has a channel or multiple channels for receiving a surgical instrument. When multiple channels are present, all the channels can run in the same direction, (e.g. the channels run in the anterolateral direction), or the channels can run in different directions, (e.g. a first channel runs in the anterior-posterior direction and a second channel runs in the lateral direction).

If the implant is made of metal, the end member is made of the same material in order to resist corrosion. The end member may also be made of allograft bone. The end member may have a wedge-shaped or spherical profile to restore the natural curvature of bone or to correct for a non-orthogonal osteotomy. One way to create the wedge-shaped profile is to have the first end of the first portion to be thicker than the second end.

The top surface can be made in any suitable cross-sectional shape, such as oval, oblong, or round, and may be annular or solid. The top surface can be a flat planar surface or can have a curvature that mimics the topography of the bone. The top surface may be provided with teeth or textured for interlocking with the bone. The teeth may have a pyramid or saw tooth shape.

In order to secure the end member to the implant, the second portion may have a hole for receiving a fastener. Alternatively, the exterior surface of the second portion may have protuberances that are sized to fit within the apertures of the implant. In an exemplary embodiment, the second portion comprises a plurality of tabs to secure the end member to the implant. These tabs may be resilient so that the tabs flex inward upon insertion of the second portion into the implant and flex back outward to create a friction fit that secures the end member to the implant. In another embodiment, the end member includes a projection hinged or pivotably connected to the first portion, a threaded bore in the second portion, and a set screw insertable into the threaded bore. Threading the set screw into the bore causes outward movement of the projection to thereby secure the end member to the implant.

In an alternative embodiment, an end member according to the present invention includes a top surface conforming in size and shape with the bone and a sleeve extending from the top surface and configured and dimensioned to receive an end of the implant. The end member further comprises first and second portions pivotable between and open position to facilitate receiving the end of the implant by the sleeve and a closed position to secure the end member to the implant. A locking element fixes the end member in the closed position.

In another alternative embodiment, the end member includes an outer ring having a prong with a ramped surface and an inner ring rotatable with respect to the outer ring. The inner ring has a protrusion which contacts the ramped surface of the prong upon rotation to thereby urge the prong radially outward.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
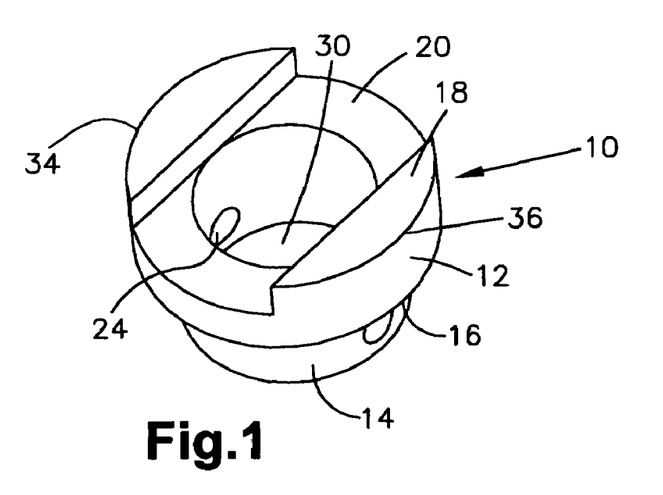
FIG. 1 shows a perspective view of a first embodiment of an end member according to present invention.

FIG. 1 shows a first embodiment of an end member 10 according to the present invention. End member 10 has a first portion 12 and a second portion 14. As first portion 12 is larger than second portion 14, a shoulder 16 is formed at the intersection between first and second portions 12, 14. A top surface 18 of first portion 12 is provided with a first slot 20 for accommodating surgical instrumentation such as holding, insertion, and/or distraction instruments. Top surface 18 is shown in FIG. 1 with a round shape. However, as will be evident from the other embodiments, top surface 18 can have any suitable shape. Preferably, top surface 18 has a shape that matches the shape of the bone it will contact.

Figure 2:
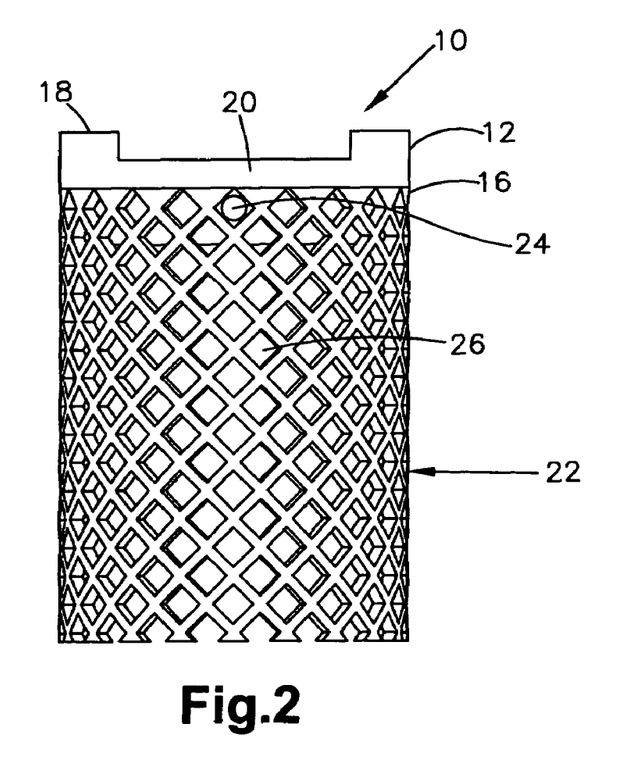
FIG. 2 shows a side view of the end member of FIG. 1 inserted into a cylindrical mesh implant.
Figure 6:
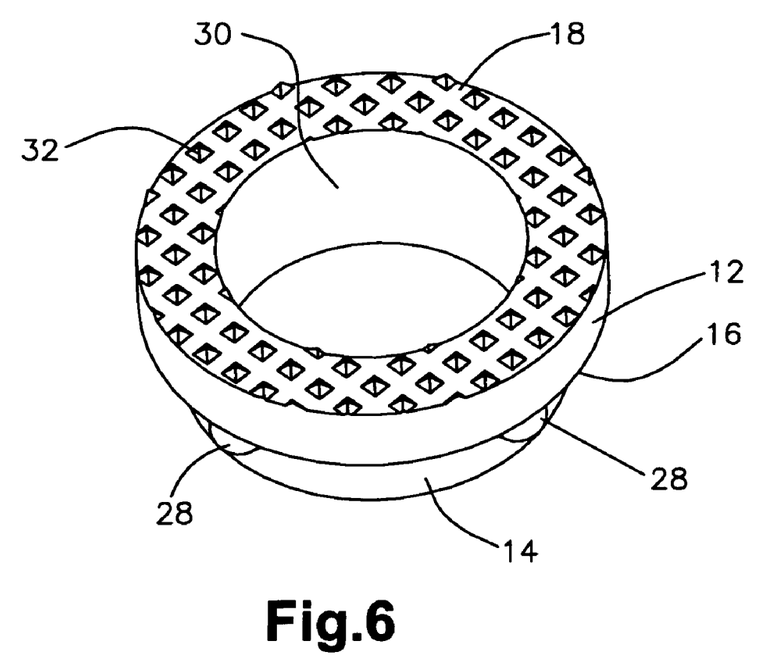
FIG. 6 shows a perspective view of an end member having protuberances for fixation to the implant.
Figure 7:
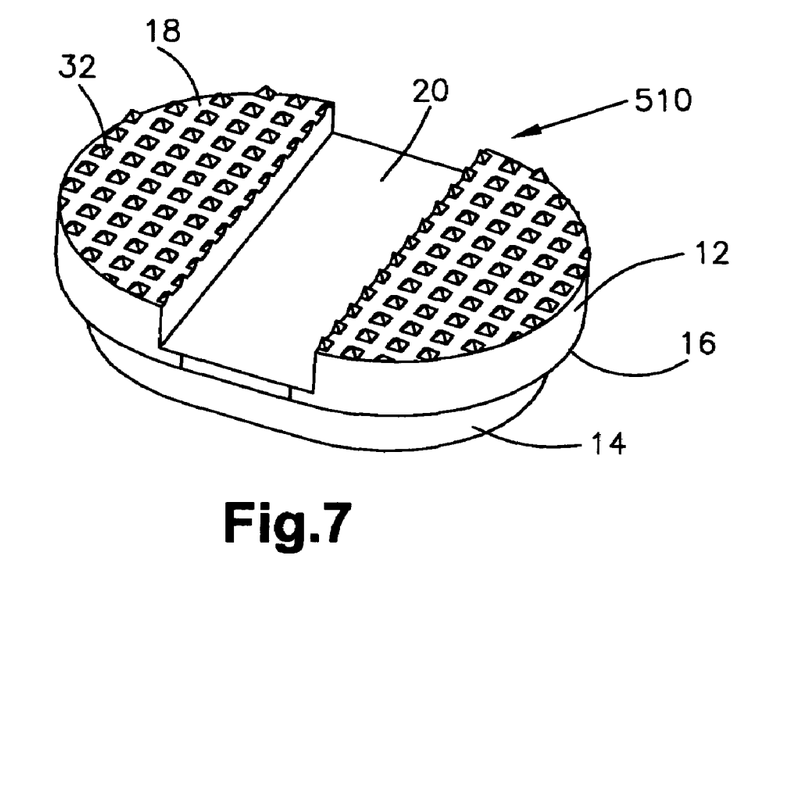
FIG. 7 shows a perspective view of a non-annular end member.

Second portion 14 is also shown having a round shape. As was the case for top surface 18, second portion 14 can have any suitable shape. Preferably, the shape of second portion 14 matches the shape of the bone fusion implant used with the end member. As best seen in FIG. 2, second portion 14 is sized and shaped to be inserted into the inner bore of a bone fusion implant 22 so that shoulder 16 rests on bone fusion implant 22. Bone fusion implant 22 can be a number of different implant types, including, for example, a mesh implant, an allograft implant, or any metallic or non-metallic implant. If implant 22 is made of a metallic material, end member 10 is preferably made of the same metallic material or a non-metallic material to avoid mixed-metal (galvanic) corrosion. End member 10 can also be made of allograft bone from cancellous bone, cortical bone, a combination of cancellous and cortical bone, or a composite of cancellous and cortical bone. After implantation of end member 10 and bone fusion implant 22, physiological compressive forces will tend to hold end member 10 in place against bone fusion implant 22. However, to provide further stability as well as to facilitate pre-operative and intra-operative handling, second portion 14 can be secured to bone fusion implant 22. For example, second portion 14 can be press-fit or snap-fit into bone fusion implant 22. Additionally, because bone fusion implant 22 is typically deformable, bone fusion implant 22 can be crimped to end member 10. Second portion 14 can also be provided with a hole 24 for receiving a fastener such as a pin or a screw. End member 10 is inserted into bone fusion implant 22 so that hole 24 aligns with one of apertures 26 on bone fusion implant 22. Hole 24 can extend either partially or completely through second portion 14 and can be threaded. As shown in FIG. 6, second portion 14 can alternatively have protuberances 28 that are sized to fit in apertures 26 for mechanically securing the end member to the bone fusion implant. Other exemplary mechanisms for securing the end member to the bone fusion implant are described in more detail below Referring back to FIGS. 1 and 2, the surface area of top surface 18 is greater than the surface area of the top and bottom surfaces of bone fusion implant 22. Because of this greater surface area, there is more contact area between top surface 18 and the surrounding bone than there would be for the top and bottom surfaces of implant 22. The increase in contact area helps to resist subsidence of implant 22. The increased contact area has other benefits such as greater load sharing between end member 10 and the surrounding bone. Top surface 18 is shown as a ring with an annular space 30. New bone can form in annular space 30 to promote fusion. Annular space can be filled with bone chips or any other osteoinductive or osteoconductive material to promote the formation of bone. Alternatively, as shown in FIG. 7, top surface 18 can be a solid surface to maximize contact area between top surface 18 and the surrounding bone. A solid top surface 18 would be desirable in clinical situations in which subsidence is especially a concern.

Figure 3:
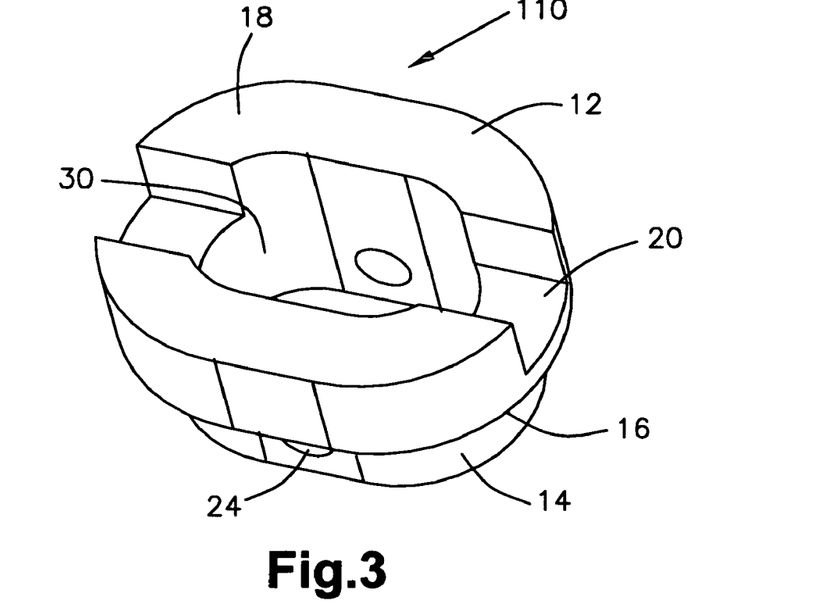
FIG. 3 shows a perspective view of an end member having an oblong shape.

FIG. 3 shows a second embodiment of an end member 110 according to the present invention. In general, most of the structure of end member 110 (as well as the embodiments described below) is like or comparable to the structure of end member 10 and, accordingly the same reference numeral is used for like components and discussion of those like components is not believed necessary. End member 110 has an oval or oblong shape and would be used in situations in which the surrounding bone (and consequently the bone fusion implant) is substantially oval or oblong. When the end member has a non-symmetrical shape like end member 110, first slot 20 can be provided in any orientation. For example, first slot 20 is shown running along the long axis of end member 110, but could run in any direction to be oriented differently with respect to the surrounding bone. The variability in the placement of first slot 20 means that first slot 20 can be positioned as best suited for the particular surgical approach that is being used. Specifically, if end member 110 is being implanted with the short axis in the anterior/posterior direction, then first slot 20 is ideal for a lateral surgical approach. If an anterior or posterior approach is anticipated, then first slot 20 should run in the anterior-posterior direction.

Figure 4A:
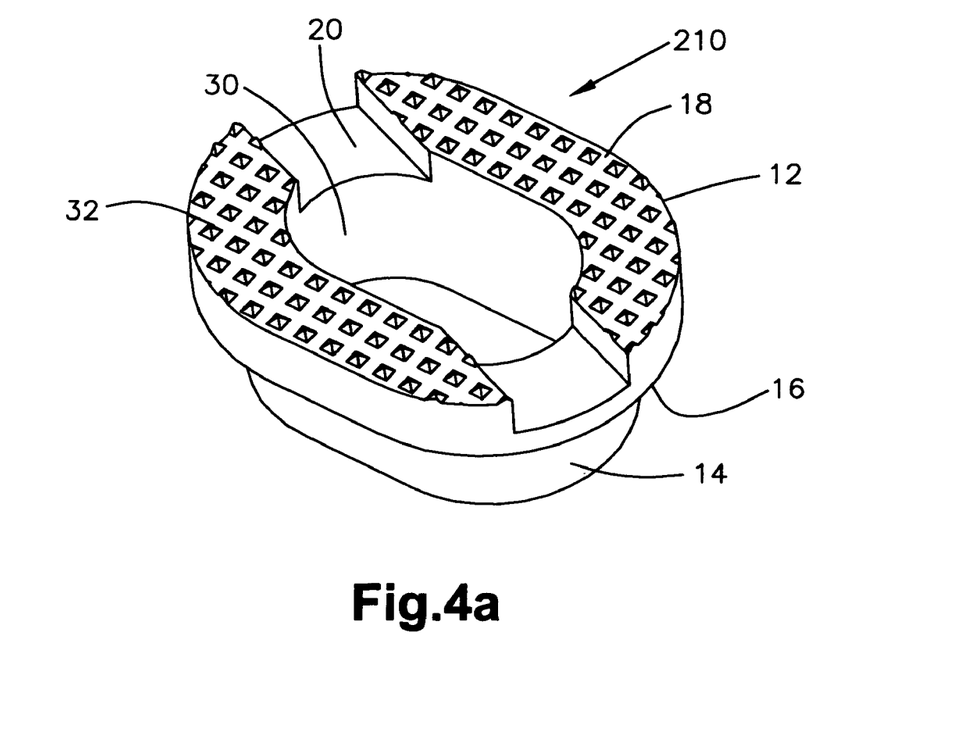
FIG. 4a shows a perspective view of an end member having an oblong shape and teeth for improving implant stability.
Figure 4B:
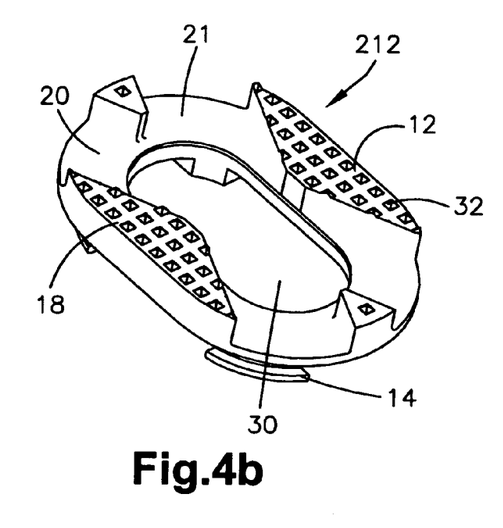
FIG. 4b shows a perspective view of an end member having first and second slots for facilitating use with implantation instrumentation.
Figure 4C:
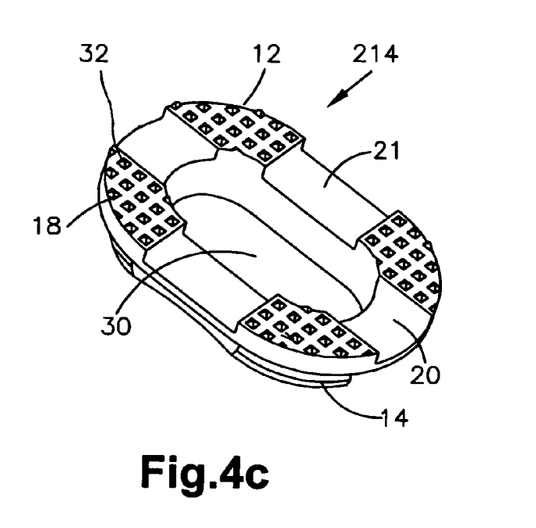
FIG. 4c shows a perspective view of another embodiment of an end member having first and second slots.

FIG. 4a shows an end member 210 with first slot 20 running at an angle with respect to the long axis of end member 210. This direction of first slot 20 is preferred for an anterolateral surgical approach, which can be used in spinal surgery. FIG. 4b shows an end member 212 that includes first and second slots 20, 21, both running at an angle with respect to the long axis of end member 212. Preferably, first and second slots 20, 21 are symmetrically placed with respect to the long axis of end member 212. Providing end member 212 with both first and second slots 20, 21 allows at least one of first and second slots 20, 21 to be accessed during implantation regardless of whether the left or right side is used for the anterolateral surgical approach. Furthermore, the arrangement of slots 20, 21 allows one end member to be used on each end of bone fusion implant and still have the slots on the top end member align with slots on the bottom end member. FIG. 4c shows an end member 214 that also includes first and second slots 20, 21. First slot 20 runs parallel to the long axis of end member 214 and second slot 21 runs transverse to the long axis of end member 214. Including both first and second slots 20, 21 on end member 214 provides access to at least one of first and second slots 20, 21 regardless of the implantation orientation of end member 214 or the surgical approach.

For each of the end members shown in FIGS. 4a, 4b, and 4c, top surface 18 has a plurality of teeth 32 which provides a mechanical interlock between the end member and the surrounding bone. Teeth 32 provide the mechanical interlock by penetrating the bone. The initial mechanical stability afforded by teeth 32 minimizes the risk of post-operative pullout or expulsion of the end member. Teeth 32 can have any suitable configuration such as pyramid-shaped, sawtooth shaped, etc. Alternatively, top surface 18 can be textured to provide the mechanical interlock between the end member and the surrounding bone.

Figure 5:
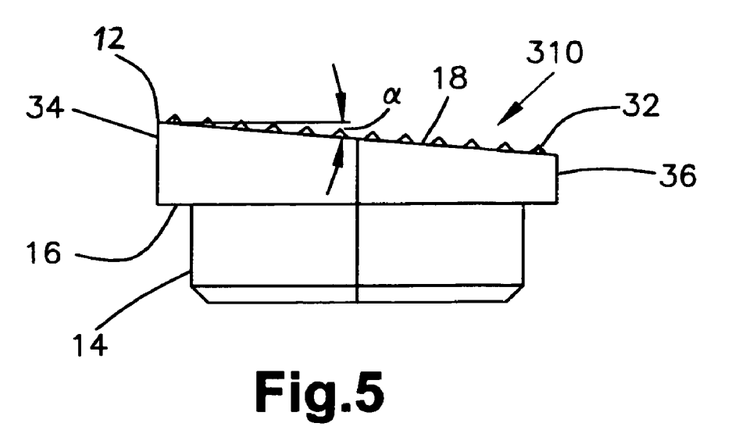
FIG. 5 shows a side view of an end member having a wedge-shape profile.

As seen in FIG. 5, an end member 310 has a wedge profile. A wedge profile would be useful in spinal applications in order to restore the natural curvature of the spine or any bone. A wedge profile would also be useful to compensate for a non-perpendicular osteotomy cut dictated by the pathology, clinical situation, or erroneously made to remove bone. It should be noted that as an end member would ordinarily be used on each end of bone fusion implant, end members having different wedge profiles can be used together. One way to achieve this wedge shape results from a gradual decrease in thickness in first portion 12 from a first end 34 to a second end 36 so that top surface 18 has a slope defined by angle $\alpha$. In FIG. 5, top surface 18 is shown as a flat planar surface. However, top surface 18 can be a curved surface and still retain the wedge-shaped profile. As the curve can be made to be a mirror-image of the topography of the vertebral end plates, a curved top surface 18 would conform to the contours of the vertebral end plates.

As previously discussed, FIG. 6 shows an end member 410 that is provided with protuberances 28 sized to fit in apertures 26 of bone fusion implant 22 (FIG. 2). FIG. 7, which has also been discussed, shows an end member 510 having a solid top surface 18 that is preferably used when there is a higher incidence of subsidence.

Figure 8:
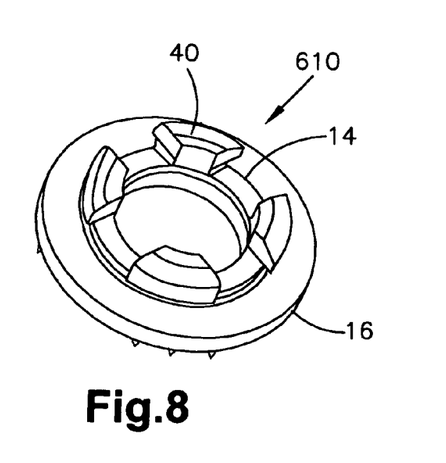
FIG. 8 shows a perspective view of the bottom of an end member according to the present invention.
Figure 9:
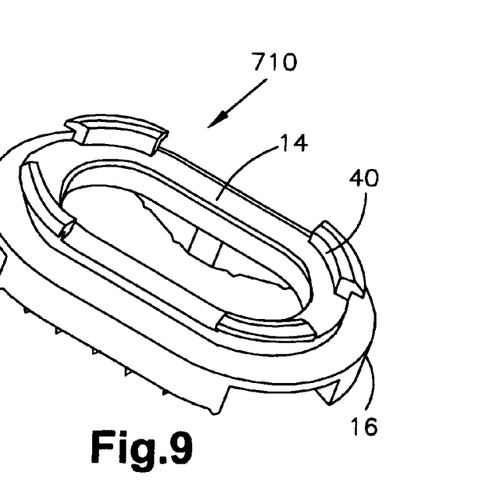
FIG. 9 shows a perspective view of the bottom of an end member according to the present invention.

FIG. 8 shows an end member 610 that has a second portion 14 that includes a plurality of tabs 40 for securing end member 610 to bone fusion implant 22. In one embodiment, tabs 40 are resilient so that as second portion 14 of end member 610 is pushed into bone fusion implant, tabs 40 flex inward and then back outward to secure end member 610 to bone fusion implant 22. As bone fusion implant 22 has some elasticity which would allow it to flex outward to accept tabs 40, tabs 40 need not be resilient. The number, size, and arrangement of tabs 40 can be varied. FIG. 9 shows an end member 710 that is similar to end member 610 except for the overall change in shape (from round to oval or oblong).

Figure 10:
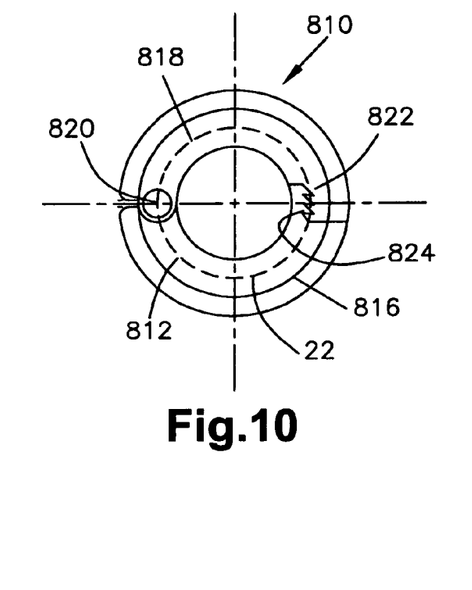
FIG. 10 shows a top view of another embodiment of the end member according to the present invention.
Figure 11:
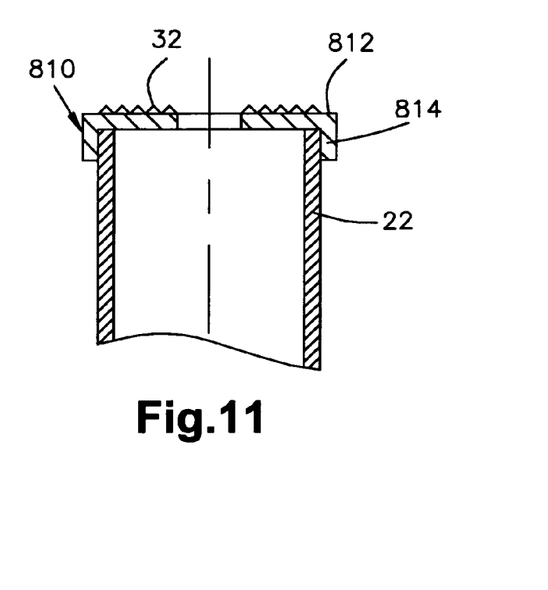
FIG. 11 shows a cross-sectional view of the end member of FIG. 10.

FIGS. 10 and 11 show an end member 810 that has another mechanism for securing end member 810 to bone fusion implant 22. Specifically, end member 810 is a cap that sits on top of implant 22. End member 810 includes a top surface 812 conforming in size and shape with the bone and a sleeve 814 extending from top surface 812. Sleeve 814 is configured and dimensioned to receive a portion of implant 22. In order to facilitate insertion and removal of end member 810 from implant 22, end member 810 is preferably made in two portions 816, 818. In an exemplary embodiment, portions 816, 818 are pivotably connected at a pivot 820 so that portions 816, 818 can be separated, i.e. end member 810 opens. End member 810 also includes a locking mechanism for keeping the two portions 816, 818 in contact. In one embodiment, this locking mechanism comprises a first serrated edge 822 that cooperates with a second serrated edge 824.

Figure 12:
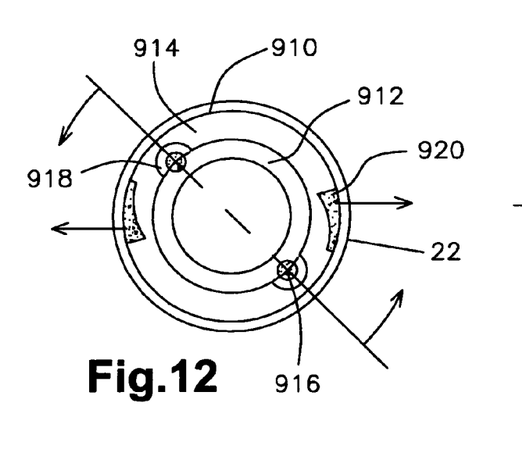
FIG. 12 shows a top view of another embodiment of the end member according to the present invention.
Figure 13:
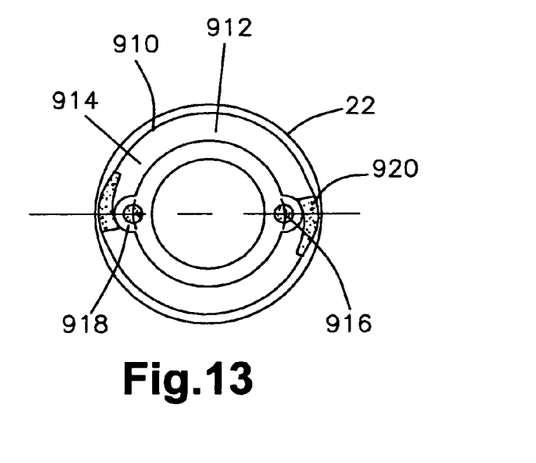
FIG. 13 shows the end member of FIG. 12 secured to a cylindrical mesh implant.

FIGS. 12 and 13 show an end member 910 that includes inner and outer rings 912, 914. Inner ring 912 can be rotated relative to outer ring 914. Inner ring 912 has means for receiving a tool to rotate inner ring 912 (shown as holes 916 that accept prongs of the tool). Inner ring 912 also has a pair of protrusions 918 that cooperate with flexible prongs 920 located on outer ring 914. As inner ring 912 is rotated, protrusions 918 contact prongs 920 and force prongs 920 out in a radial direction. When end member 910 is fitted in implant 22, the outward radial movement of prongs 920 causes prongs 920 to press against implant 22 to secure end member 910 to implant 22.

Figure 14:
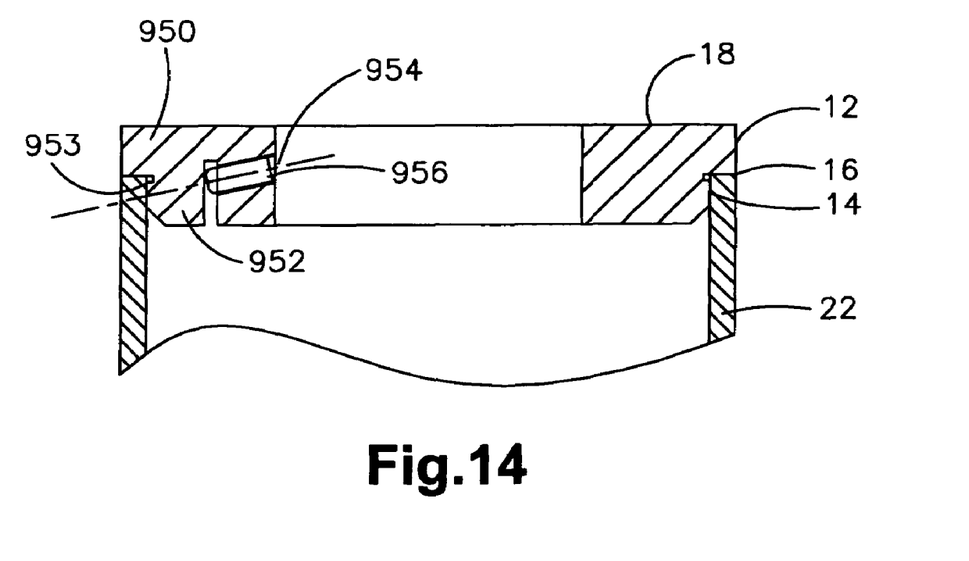
FIG. 14 shows a cross-sectional view of another embodiment of the end member according to the present invention.

FIG. 14 shows an end member 950 in which second portion 14 includes at least one projection 952. Projection 952 is pivotably connected to second portion 14 at junction 953 so that as a set screw 954 is screwed into threaded bore 956, set screw 954 causes outward movement of projection 952. This outward movement secures end member 950 to implant 22. Junction 953 preferably has a reduced cross section compared to the rest of projection 952 so that the flexing caused by set screw 954 occurs in junction 953.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

We claim:

1. A bone fusion implant comprising:
   an intervertebral spacer body; and
   at least one end member further comprising:
      a first portion with a top surface adapted and configured to engage the bone and having a perimeter edge and a first channel extending across at least a portion of the top surface from the perimeter edge for receiving a surgical instrument;
      a second portion configured and dimensioned to be inserted into a bore of the intervertebral spacer body; and
      a shoulder joining the first and second portions and sized to rest on an end edge of the intervertebral spacer body when the second portion is inserted in the bore of the intervertebral spacer body;
      wherein the second portion comprises a plurality of resilient tabs flexing inward upon insertion of the second portion in the bore of the intervertebral spacer body and flexing back outward to secure the end member to the intervertebral spacer body.

2. The implant of claim 1, wherein the intervertebral spacer body has a first outer cross-sectional dimension and the first portion has a second outer cross-sectional dimension, the first outer cross-section dimension and the second outer cross-sectional dimension are substantially identical when the second portion is inserted into The bore of the intervertebral spacer body.

3. The implant of claim 1 wherein the top surface and the intervertebral spacer body are selected from the group consisting of annular, circular, oval, and oblong.

4. The implant of claim 1 wherein the top surface has a second channel for receiving the surgical instrument.

5. The implant of claim 4 wherein the first and second channels run in an anterolateral direction.

6. The implant of claim 1 wherein the end member is made of a metal.

7. The implant of claim 1 wherein the fast portion further comprises an inside perimeter edge defining a central opening, the first channel extending from the perimeter edge to the inside perimeter edge for receiving the surgical instrument.

8. The implant of claim 7 wherein the top surface between the outer perimeter edge and the inner perimeter edge contains a plurality of teeth for providing a mechanical interlock between the top surface of the end member and the surrounding bone.

9. The end member of claim 1 wherein the end member has a longitudinal axis and a lateral axis, a dimension of the longitudinal axis being substantially identical to a dimension of the lateral axis, wherein the first channel is aligned offset from both the longitudinal and the lateral axes.

10. The end member of claim 1 wherein the end member has a major axis and a minor axis, a dimension of the major axis being larger than a corresponding dimension of the minor axis, wherein the first channel is aligned offset with the major axis.

11. The end member of claim 10 wherein the end member comprises a second channel which is aligned offset with the minor axis.

12. The end member of claim 1 wherein the second portions includes four resilient tabs.

13. An end member for use with an implant for fusing bone comprising:
    a first portion with a top surface adapted and configured to engage the bone and having an outer perimeter edge, an inside perimeter defining a central opening, a first channel extending from the outer perimeter edge to the inside perimeter edge for receiving a surgical instrument;
    a second portion configured and dimensioned to be inserted into the implant; and
    a shoulder joining the first and second portions and sized to rest on an end edge of the implant when the second portion is inserted into the implant;
    wherein the second portion comprises four resilient tabs that flex inward upon insertion of the second portion into the implant and flexing back outwards to secure the end member to the implant;
    wherein the top surface between the outer perimeter edge and the inner perimeter edge contains a plurality of teeth for providing a mechanical interlock between the top surface of the end member and the surrounding bone.

14. The end member of claim 13 wherein the top surface has a second channel for receiving the surgical instrument.

15. The end member of claim 13 wherein the implant is an intervertebral spacer body such that the resilient tabs of the second portion are sized and configured to be inserted into a bore of the intervertebral spacer body so that the end edge of the intervertebral spacer body rests against the shoulder of the end member when the second portion is inserted into the bore of the intervertebral spacer body.

16. The end member of claim 15, wherein the intervertebral spacer body has a first outer cross-sectional dimension and the first portion has a second outer cross-sectional dimension the first outer cross-sectional dimension and the second outer cross-sectional dimension are substantially identical when the second portion is inserted into the intervertebral spacer body.

17. An end member for use with an implant for fusing bone comprising:
    a first portion with a top surface adapted and configured to engage the bone and having an outer perimeter edge, an inner perimeter edge defining a central opening and a first channel extending across at least a portion of the top surface from the outer perimeter edge to the inner perimeter edge for receiving a surgical instrument, the top surface, between the outer perimeter edge and the inner perimeter edge, including a plurality of teeth for providing a mechanical interlock between the top surface of the end member and the surrounding bone;
    a second portion configured and dimensioned to be inserted into a bore of the implant; and
    a shoulder joining the first and second portions and sized to rest on an end edge of the implant when the second portion is inserted in the bore of the implant;
    wherein the second portion comprises a plurality of resilient tabs flexing inward upon insertion of the second portion in the implant and flexing back outward to secure the end member to the implant.

18. The end member of claim 17, wherein the plurality of teeth are provided in a two dimensional array with the teeth being spaced apart from one another.

19. The end member of claim 17, wherein the first portion has a shape selected from the group consisting of annular, circular, oval, and oblong.

20. The end member of claim 17, wherein the top surface has a second channel for receiving the surgical instrument.

21. The end member of claim 17, wherein the implant is an intervertebral spacer body such that the resilient tabs of the second portion are sized and configured to be inserted into the intervertebral spacer body so that the end edge of the intervertebral spacer body rests against the shoulder of the end member when the second portion is inserted into the intervertebral spacer body.

22. The end member of claim 21, wherein the intervertebral spacer body has a first outer cross-sectional dimension and the first portion has a second outer cross-sectional dimension, the first outer cross-sectional dimension and the second outer cross-sectional dimension are substantially identical when the second portion is inserted into the intervertebral spacer body.

23. An end member for use with an implant for fusing bone comprising:
    a first portion with a top surface adapted and configured to engage the bone and having a perimeter edge and a first channel extending across at least a portion of the top surface from the perimeter edge for receiving a surgical instrument, the top surface further including a plurality of teeth provided in a two dimensional array with the teeth being spaced apart from one another for interlocking with the bone;
    a second portion configured and dimensioned to be inserted into a bore of the implant; and a shoulder joining the first and second portions and sized to rest on an end edge of the implant when the second portion is inserted in the bore of the implant;

wherein the second portion comprises a plurality of resilient tabs flexing inward upon insertion of the second portion in the implant and flexing back outward to secure the end member to the implant.

24. The end member of claim 23, wherein the top surface further includes an inner perimeter edge defining a central opening and the first channel extends from the perimeter edge to the inner perimeter edge for receiving the surgical instrument.

25. The end member of claim 23, wherein the first portion has a shape selected from the group consisting of annular, circular, oval, and oblong.

26. The end member of claim 23, wherein the top surface has a second channel for receiving the surgical instrument.

27. The end member of claim 23, wherein the implant is an intervertebral spacer body such that the resilient tabs of the second portion are sized and configured to be inserted into the intervertebral spacer body so that the end edge of the intervertebral spacer body rests against the shoulder of the end member when the second portion is inserted into the intervertebral spacer body.

28. The end member of claim 27, wherein the intervertebral spacer body has a first outer cross-sectional dimension and the first portion has a second outer cross-sectional dimension, the first outer cross-sectional dimension and the second outer cross-sectional dimension are substantially identical when the second portion is inserted into the intervertebral spacer body.

* * * * *